United States Patent [19]

Theodoridis

[11] Patent Number: 5,346,881
[45] Date of Patent: Sep. 13, 1994

[54] 2-(BICYCLIC HETEROCYCLYL)-6-FLUOROALK-YLURACILS

[75] Inventor: George Theodoridis, Princeton, N.J.

[73] Assignee: FMC Corporation, Philadelphia, Pa.

[21] Appl. No.: 107,097

[22] Filed: Aug. 13, 1993

[51] Int. Cl.$^5$ .................... A01N 43/48; C07D 239/55
[52] U.S. Cl. .................... 504/243; 544/310; 549/362
[58] Field of Search .................... 544/310; 504/243; 549/362

[56] References Cited

U.S. PATENT DOCUMENTS

| | | | |
|---|---|---|---|
| 3,235,358 | 2/1966 | Soboczenski | 544/309 |
| 3,235,362 | 2/1966 | Ellis | 544/309 |
| 3,330,640 | 7/1967 | Luckenbaugh | 544/309 |
| 4,193,787 | 3/1980 | Baker | 549/362 |
| 4,423,237 | 12/1983 | Baker | 549/362 |
| 4,981,508 | 1/1991 | Strunk et al. | 544/310 |
| 5,127,935 | 7/1992 | Satow et al. | 544/310 |
| 5,154,755 | 10/1992 | Satow et al. | 544/310 |
| 5,169,430 | 12/1992 | Strunk et al. | 544/309 |
| 5,183,492 | 2/1993 | Suchy et al. | 544/309 |

FOREIGN PATENT DOCUMENTS

| | | |
|---|---|---|
| 476697A | 9/1991 | European Pat. Off. . |
| 2468603 | 5/1981 | France .................... 544/310 |

OTHER PUBLICATIONS

Derwent Accession No. 91-216895-Published European Patent Application No. EP 438,209A (Jan. 18, 1990).
Derwent Accession No. 93-216895-Published World Patent Application No. WO 9314073-A1 (Jan. 20, 1992).

Primary Examiner—Cecilia Tsang
Attorney, Agent, or Firm—Robert L. Andersen; H. Robinson Ertelt

[57] ABSTRACT

Herbicidal 3-(bicyclic heterocyclyl)-6-fuoroalkyluracils of the formula

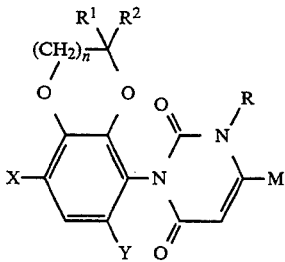

in which M is fluoroalkyl($C_{1-6}$); R is hydrogen, alkyl($C_{1-6}$), 2-alkynyl($C_{3-6}$); 2-alkenyl($C_{3-6}$,), or cyanoalkyl($C_{1-6}$); $R^1$ is hydrogen or alkyl($C_{1-6}$); $R^2$ is hydrogen or alkyl ($C_{1-6}$); Y is hydrogen, fluorine, chlorine, or bromine; X is hydrogen, fluorine, chlorine, bromine, cyano, alkyl($C_{1-6}$), or fluoroalkyl($C_{1-6}$); and n is 0 or 1.

13 Claims, No Drawings

2-(BICYCLIC HETEROCYCLYL)-6-FLUOROALKYLURACILS

This invention relates to uracil compounds which are useful as herbicides, and intermediates which are useful for producing herbicides. More particularly the present invention pertains to 3-(bicyclic heterocyclyl)-1-substituted-6-fluoroalkyluracils, methods of preparing them, their intermediates, their compositions, and methods of destroying unwanted plants by preemergence or postemergence application of the herbicidal compositions to the locus where control is desired. The herbicidal compounds of this invention may be used to effectively control a variety of grassy or broad leaf plant species.

One aspect of this invention relates to compounds of the formula:

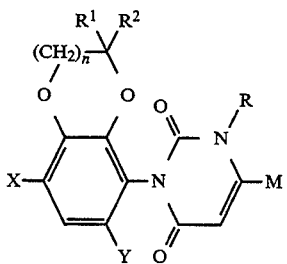

in which
- M is fluoroalkyl ($C_{1-6}$, preferably $C_{1-3}$, more preferably $C_1$) having 1 to 6 fluorines;
- R is hydrogen, alkyl($C_{1-6}$, preferably $C_{1-3}$, more preferably $C_1$), 2-alkynyl($C_{3-6}$, preferably $C_{3-4}$, more preferably $C_3$), and 2-alkenyl($C_{3-6}$, preferably $C_{3-4}$, more preferably $C_3$), or cyanoalkyl($C_{1-6}$, preferably $C_{1-3}$, more preferably $C_1$) having one or two cyano groups;
- $R^1$ is hydrogen or alkyl($C_{1-6}$, preferably $C_{1-3}$; more preferably $C_1$);
- $R^2$ is hydrogen or alkyl($C_{1-6}$, preferably $C_{1-3}$; more preferably $C_1$);
- Y is hydrogen, fluorine, chlorine, or bromine;
- X is hydrogen, fluorine, chlorine, bromine, cyano, alkyl($C_{1-6}$, preferably $C_{1-3}$, more preferably $C_1$), or fluoroalkyl($C_{1-6}$, preferably $C_{1-3}$, more preferably $C_1$) having 1 to 6 fluorines; and
- n is 0 or 1.

Preferred compounds include those in which M is trifluoromethyl or pentafluoroethyl; R is methyl or ethyl; $R^1$ is hydrogen, methyl, or ethyl; $R^2$ is hydrogen, methyl, or ethyl; X is chlorine or bromine; Y is hydrogen, chlorine, or fluorine; and n is 0 or 1. Compounds which are more preferred include those in which M is trifluoromethyl; R is methyl; $R^1$ is hydrogen or methyl; $R^2$ is hydrogen or methyl; X is chlorine or bromine; Y is hydrogen, chlorine, or fluorine; and n is 0 or 1.

Compounds which are particularly preferred include 3-(7-chloro-2,2-dimethyl-5-fluoro-1,3-benzodioxol-4-yl)- 1 -methyl-6-trifluoromethyluracil; 3(7-bromo-2,2-dimethyl-5-fluoro-1,3-benzodioxol-4-yl)-1 -methyl-6-trifluoromethyluracil; 3-(8-chloro-1,4-benzodioxan-5-yl)- 1 -methyl-6-trifluoromethyluracil; 3-(8-bromo-6-fluoro-1,4-benzodioxan-5-yl)- 1 -methyl-6-trifluoromethyluracil; 3-(8-chloro-6-fluoro-1,4-benzodioxan-5-yl)-1 -methyl-6-trifluoromethyluracil; 3-(6,8-dichloro-1,4-benzodioxan-5-yl)-1 -methyl-6-trifluoromethyluracil; and 3-(7-chloro-2,2-dimethyl-1,3-benzodioxol-4-yl)-1-methyl-6-trifluoromethyluracil.

Representative compounds of this invention are listed in Table 1. Characterizing properties of various compounds are listed in Table 2

Using commercially available starting materials or those whose synthesis is known in the art, the compounds of this invention may be prepared using methods described in the following Examples and Schema, or using modifications thereof which are within the skill of the art.

The 3-(1,3-benzodioxol-4-yl)-6-fluoroalkyluracils of this invention may be synthesized by first reacting a 1,2-dimethoxybenzene, for example, 1,2-dimethoxy-4-fluorobenzene, with boron tribromide to give the corresponding 1,2-dihydroxybenzene. The dihydroxybenzene and a ketone or aldehyde, for example, acetone, are then reacted with phosphorous pentoxide to yield the 1,3-benzodioxole. The corresponding 1,3-benzodioxol-4-carboxylic acid is produced by treating the 1,3-benzodioxole with n-butyl lithium after which carbon dioxide is introduced into the reaction mixture. The tertiary butyl N-(1,3-benzodioxol-4-yl)carbamate is then prepared from the acid and t-butanol in the presence of diphenylphosphoryl azide. The carbamate is cleaved by stirring it in trifluoroacetic acid to give the corresponding 4-amino-1,3,benzodioxole, for example, 4-amino-2,2-dimethyl-5-fluoro-1,3-benzodioxole. The 4-amino-1,3-benzodioxole may be chlorinated in the 7-position using N-chlorosuccinimide in dimethylformamide. The dioxole is then converted to the corresponding isocyanate by reaction with trichloromethyl chloroformate. The isocyanate may be used in the next reaction without purification where it is reacted with sodium hydride and a 3-amino-3-fluoroalkylacrylate, for example, 3-amino-4,4,4-trifluorocrotonate, to produce the 3-( 1,3-benzodioxol-4-yl)-6-haloalkyluracil, for example, 3-(7-chloro-2,2-dimethyl-5-fluoro- 1,3-benzodioxol-4-yl)-6-trifluoromethyluracil. This compound may be isolated or, alternatively, reacted with an alkyl iodide and potassium carbonate without isolation to produce the 3-(1,3-benzodioxol-4-yl)-1-alkyl-6-haloalkyluracil, for example, 3-(7-chloro-2,2-dimethyl-5-fluoro-1,3-benzodioxol-4-yl)-1-methyl-6-trifluoromethyluracil. Example 1 provides details of this synthetic procedure.

The 3-(1,4-benzodioxan-5-yl)uracils of this invention may be synthesized, for example, by first reacting a 5-amino-1,4-benzodioxane such as 5-amino-6-fluoro-1,4-benzodioxane with an N-halosuccinimide to give, for example, 5-amino-8-bromo-6-fluoro-1,4-benzodioxane. The method of producing the corresponding isocyanate by reacting the 1,4-benzodioxane with a 3-amino-3-fluoroalkylacrylate and subsequently with an alkyl iodide and potassium carbonate is the same as previously described for the 1,3-benzodioxoles. Example 2 gives details of this synthetic route.

Examples 3, 4, and 5 all start with Compound 17, 3-(7-bromo-2,2-dimethyl-5-fluoro- 1,3-benzodioxol-4-yl)- 1 -methyl-6-trifluoromethyluracil. In these Examples, the 7-bromo substituent is replaced with a methyl group, a trifluoromethyl group, and a cyano group. To introduce the 7-methyl group, the procedure of M. Kosugi et al., *Chem. Letters* (1977), 301 is used by reacting tetramethyl tin with the uracil in an aromatic solvent in the presence of tetrakis(triphenylphosphine)palladium(O) in a sealed tube at 120 ° C. In order to introduce a trifluoromethyl group into the same position, the 7-bromo compound is heated with copper(I) iodide and sodium trifluoroacetate in N,N-dimethylacetamide, according to the method of G. Theodoridis et al., *Pestic. Sci.* (1990), 30, 259. A mixture of the 7-bromo compound and copper(I) cyanide in N,N-dimethylformamide is heated at reflux and is then poured into a mixture of hydrated ferric chloride, hydrochloric acid and water to introduce the cyano group into the molecule. This is the method of A. C. Cheng and N. Castagnoli, *J. Med. Chem,* 27(4), 513(1984).

Example 1

SYNTHESIS OF 3-(7-CHLORO-2,2-DIMETHYL-5-FLUORO-1,3-BENZODIOXOL-4-YL)- 1 -METHYL-6-TRIFLUOROMETHYLURACIL (Compound 5)

Step A Synthesis of 1,2-dihydroxy-4-fluorobenzene

A 1 M solution of boron tribromide in methylene chloride (500 mL, 0.50 mole) was cooled to −78 ° C. To this solution was added in a dropwise manner a solution of 46 g (0.30 mole) of 1,2-dimethoxy-4-fluorobenzene in 100 mL of methylene chloride. Upon completion of addition, the mixture was allowed to warm to ambient temperature at which it stirred for about 16 hours. At the conclusion of this period the reaction mixture was cooled to 0° C., and ethanol was added to the reaction mixture. The solvents were evaporated under reduced pressure, leaving 40 g of 1,2-dihydroxy-4-fluorobenzene as a residue. The NMR spectrum was consistent with the proposed structure.

Step B Synthesis of 2,2-dimethyl-5-fluoro- 1,3-benzodioxole

In a flask were placed 40 g (0.31 mole) of 1,2-dihydroxy-4-fluorobenzene, 36.25 g (0.625 mole) of acetone, and 400 mL of methylene chloride. To this solution was added 133 g (0.937 mole) of phosphorus pentoxide in portions during a five minute period. This mixture was stirred at ambient temperature for approximately 16 hours after which the methylene chloride was decanted from the solid material in the flask. Ice was added to the flask, and the solid residue was dissolved in water and extracted with methylene chloride. The phases were separated, and the organic phase was combined with the methylene chloride solution that had been decanted from the reaction mixture. This solution was washed in succession with a 5% aqueous solution of sodium hydroxide and then with water. After being dried over anhydrous magnesium sulfate and filtered, the organic solution was evaporated under reduced pressure, leaving 29.3 g of 2,2-dimethyl-5-fluoro-1,3-benzodioxole as a residue. The NMR spectrum was consistent with the proposed structure.

Step C Synthesis of 2,2-dimethyl-5-fluoro-1,3-benzodioxol-4-ylcarboxylic acid

In a flask were placed 29.3 g (0.174 mole) of 2,2-dimethyl-5-fluoro-1,3-benzodioxole and 200 mL of dry tetrahydrofuran, and the resulting solution was cooled to −78° C. To this solution was added dropwise 66.4 mL (0.166 mole) of a 2.5 M solution of n-butyllithium in hexanes. This mixture was stirred at −78° C. for one hour after which a carbon dioxide atmosphere was placed above the reaction mixture. The temperature was allowed to warm to ambient conditions during a 16 hour period while maintaining the carbon dioxide atmosphere. At the conclusion of this period the solvent was evaporated under reduced pressure, and diethyl ether was added to the residue. This mixture was extracted with water, and the water extract was in turn extracted with diethyl ether. The aqueous phase was separated and acidified with hydrochloric acid. The acidified mixture was then extracted with methylene chloride. The methylene chloride extract was washed with water, dried over anhydrous magnesium sulfate, and filtered. The filtrate was evaporated under reduced pressure, leaving 19 g of 2,2-dimethyl-5-fluoro-1,3-benzodioxol-4-ylcarboxylic acid as the residue. The NMR spectrum was consistent with the proposed structure.

Step D Synthesis of t-butyl N-(2,2-dimethyl-5-fluoro-1,3-benzodioxol-4-yl)carbamate In a flask were placed 10 g (0.047 mole) of 2,2-dimethyl-5-fluoro-1,3-benzodioxol-4-ylcarboxylic acid, 12.98 g (0.0471 mole) of diphenylphosphoryl azide, 4.77 g (0.0471 mole) of triethylamine, and 80 mL of t-butanol. This mixture was heated at reflux for approximately 16 hours, after which the solvent was evaporated under reduced pressure. The residue was passed through a column of silica gel, eluting first with a ;methylene chloride/heptane mixture and finally with pure methylene chloride. The product-containing fractions were combined, and the solvents were evaporated under reduced pressure, leaving 11.9 g of t-butyl N-(2,2-dimethyl-5-fluoro-1,3-benzodioxol-4-yl)carbamate as a residue, mp 106–107° C. The NMR spectrum was consistent with the proposed structure.

Step E Synthesis of 4-amino-2,2-dimethyl-5-fluoro- 1,3-benzodioxole

In a flask was placed 50 mL of trifluoroacetic acid which was cooled to 0° C. To this cooled trifluoroacetic acid was added 11.5 g (0.041 mole) of t-butyl N-(2,2-dimethyl-5-fluoro-1,3-benzodioxol-4-yl)carbamate. This mixture was allowed to warm to ambient temperature at which it was stirred for 90 minutes. Diethyl ether and water were added to the mixture which was made basic with sodium bicarbonate. The organic phase was separated from the aqueous phase, and the former was dried with anhydrous magnesium sulfate and filtered. The filtrate was concentrated under reduced pressure, and the residue was passed through a column of silica gel, eluting with methylene chloride/heptane (1:1). Product-containing fractions were combined and the solvent evaporated under reduced pressure, yielding 4.9 g of 4-amino-2,2-dimethyl-5-fluoro-1,3-benzodioxole as the residue. The NMR spectrum was consistent with the proposed structure.

Step F Synthesis of 4-amino-7-chloro-2,2-dimethyl-5-fluoro- 1,3-benzodioxole

In a flask were placed 2.23 g (0.0122 mole) of 4-amino-2,2-dimethyl-5-fluoro-1,3-benzodioxole and 40 mL of N,N-dimethylformamide. To this solution was added in a dropwise manner a solution of 1.79 g (0.0134 mole) of N-chlorosuccinimide in N,N-dimethylformamide while maintaining the temperature at ambient conditions. The solvent was evaporated under reduced pressure, leaving a residue which was passed through a column of silica gel eluting with methylene chloride/heptane (1:1 ). Product-containing fractions were combined and the solvent evaporated, yielding 1.93 g of 4-amino-7-chloro-2,2-dimethyl-5-fluoro-1,3-benzodioxole as the residue. The NMR spectrum was consistent with the proposed structure.

Step G Synthesis of 7-chloro-2,2-dimethyl-5-fluoro-1,3-benzodioxol-4-yl isocyanate To a solution of 1.5 g (0.0069 mole) of 4-amino-7-chloro-2,2-dimethyl-5-fluoro-1,3-benzodioxole in 50 mL of toluene was added slowly 0.41 mL (0.0035 mole) of trichloromethyl chloroformate. This mixture was stirred at ambient temperature for one hour and then was heated at reflux for approximately 16 hours. At the conclusion of this period the solvent was evaporated from the reaction mixture under reduced pressure, leaving 7-chloro-2,2-dimethyl-5-fluoro-1,3-benzodioxol-4-yl isocyanate as a residue which was used in the next step without further purification.

Step H Synthesis of 3-(7-chloro-2,2-dimethyl-5-fluoro-1,3-benzodioxol-4-yl)- 1 -methyl-6-trifluoromethyluracil A mixture of 0.32 g (0.0079 mole) of sodium hydride and 200 mL of dry tetrahydrofuran was cooled to -20 ° C, and 1.26 g (0.0069 mole) of ethyl 3-amino-4,4,4-trifluorocrotonate was added in a dropwise manner. This mixture was stirred for 10 minutes, and then 1.68 g (0.0069 mole) of 7-chloro-2,2-dimethyl-5-fluoro-1,3-benzodioxol-4-yl isocyanate was added in a dropwise manner. Upon completion of addition, the reaction mixture was allowed to warm to ambient temperature at which it was stirred for one hour. At the conclusion of this period the reaction mixture was heated to 85 ° C. at which it was stirred for approximately 16 hours. Then 0.95 g (0.0069 mole) of potassium carbonate and 1.96 g (0.0138 mole) of methyl iodide were added to the reaction mixture, and it was heated at 75 ° C for seven hours. At the conclusion of this period, water was added to the reaction mixture, and the resulting mixture was extracted with diethyl ether. The extracts were washed with water, dried over anhydrous magnesium sulfate, filtered, and the solvent evaporated from the filtrate under reduced pressure, leaving a residue. This residue was passed through a column of silica gel, eluting with ethyl acetate:heptane (4:1). Product-containing fractions were combined, and the solvent was evaporated under reduced pressure, leaving 0.58 g of 3-(7-chloro-2,2-dimethyl-5-fluoro- 1,3-benzodioxol-4-yl)-1 -methyl-6-trifluoromethyluracil (Compound 5) as an oil. The NMR spectrum was consistent with the proposed structure.

Example 2

SYNTHESIS OF 3-(8-CHLORO-6-FLUORO-1,4-BENZODIOXAN-4-YL)-1-METHYL-6-TRIFLUOROMETHYLURACIL (Compound 21)

Step A Synthesis of 5-amino-8-chloro-6-fluoro-1,4-benzodioxane

In a flask were placed 3.05 g (0.018 mole) of 5-amino-6-fluoro-1,4-benzodioxane and 40 mL of N,N-dimethylformamide. To this solution was added in a dropwise manner a solution of 2.65 g (0.0198 mole) of N-chlorosuccinimide in N,N-dimethylformamide while maintaining the temperature at ambient conditions. The solvent was evaporated under reduced pressure, leaving a residue which was passed through a column of silica gel, eluting with methylene chloride/heptane (1:1). Product-containing fractions were combined and the solvent evaporated, yielding 2.25 g of 5-amino-8-chloro-6-fluoro-1,4-benzodioxane as the residue. The NMR spectrum was consistent with the proposed structure.

Step B Synthesis of 8-chloro-6-fluoro-1,4-benzodioxan-5-yl isocyanate

To a solution of 2.25 g (0.011 mole) of 5-amino-8-chloro-6-fluoro-1,4-benzodioxane in 50 mL of toluene was added slowly 0.67 mL (1.09 g, 0.0055 mole) of trichloromethyl chloroformate. This mixture was stirred at ambient temperature for one hour and then was heated at reflux for approximately 16 hours. At the conclusion of this period the solvent was evaporated from the reaction mixture under reduced pressure, leaving 8-chloro-6-fluoro-1,4-benzodioxan-5-yl isocyanate as a residue which was used in the next step without further purification.

Step C Synthesis of 3-(8-chloro-6-fluoro- 1,4-benzodioxan-5-yl)-1-methyl-6-trifluoromethyluracil A mixture of 0.44 g (0.011 mole) of sodium hydride and 200 mL of dry tetrahydrofuran was cooled to −20 ° C, and 2.03 g (0.011 mole) of ethyl 3-amino-4,4,4-trifluorocrotonate was added in a dropwise manner. This mixture was stirred for 10 minutes, and then 2.53 g (0.011 mole) of 8-chloro-6-fluoro-1,4-benzodioxan-4-yl isocyanate was added in a dropwise manner. Upon completion of addition, the reaction mixture was allowed to warm to ambient temperature at which it was stirred for one hour. At the conclusion of this period the reaction mixture was heated to 85 ° C at which it was stirred for approximately 16 hours. Then 1.53 g (0.011 mole) of potassium carbonate and 3.14 g (0.022 mole) of methyl iodide were added to the reaction mixture, and it was heated at 75 ° C for seven hours. At the conclusion of this period water was added to the reaction mixture, and the resulting mixture was extracted with diethyl ether. The extracts were washed with water, dried over anhydrous magnesium sulfate, filtered, and the solvent evaporated from the filtrate under reduced pressure, leaving a residue. This residue was passed through a column of silica gel, eluting first with heptane and then with ethyl acetate:heptane (1:3). Product-containing fractions were combined, and the solvent was evaporated under reduced pressure, leaving 2.3 g of 3-(8-chloro-6-fluoro-1,4-benzodioxan-4-yl)-1-methyl-6-trifluoromethyluracil (Compound 21 ), mp 186–190. The NMR spectrum was consistent with the proposed structure.

Example 3

SYNTHESIS OF 3-(2,2-DIMETHYL-5-FLUORO-7-METHYL-1,3-BENZODIOXOL-4-YL)- 1 -METHYL-6-TRIFLUOROMETHYLURACIL (Compound 12)

Synthesis of this compound starts with 3-(7-bromo-2,2-dimethyl-5-fluoro-1,3-benzodioxol-4-yl)-1-methyl-6-trifluoromethyluracil (Compound 17) which may be synthesized using the methods of Example 1, Steps F through H, by substituting N-bromosuccinimide for N-chlorosuccinimide in Step F. In a tube are placed 2.2 g (0.005 mole) of 3-(7-bromo-2,2-dimethyl-5-fluoro-1,3-benzodioxol-4-yl)- 1 -methyl-6-trifluoromethyluracil, 0.95 g (0.0053 mole) of tetramethyl tin, 0.05 g (0.00005 mole) of tetrakis(triphenylphosphine)palladium(0), and 3 mL of xylene. The tube is sealed and heated at 120 ° C for approximately 20 hours after which it is cooled, the seal is broken, and the contents are removed. The reaction mixture is passed through a column of silica gel, eluting with heptane/ethyl acetate ( 1:1 ). The product-containing fractions are combined, and the solvent is evaporated under reduced pressure, yielding 3-(2,2-dimethyl-5-fluoro-7-methyl- 1,3-benzodioxol-4-yl)- 1 -methyl-6-trifluoromethyluracil as the residue.

Example 4

SYNTHESIS OF-(2,2-DIMETHYL-5-FLUORO-7-TRI-FLUOROMETHYL-1,3-BENZODIOXOL-4-YL)- 1 -METHYL-6-TRIFLUOROMETHYLURACIL (Compound 13)

To a solution of 6.0 g (0.044 mole) of sodium trifluoroacetate, 4.18 g (0.022 mole) of copper(I)iodide, and 40 mL of N,N-dimethylacetamide under a nitrogen atmosphere at 140 °C is added 4.83 g (0.011 mole) of 3-(7-bromo-2,2-dimethyl-5-fluoro- 1,3-benzodioxol-4-yl)- 1 -methyl-6-trifluoromethyluracil (Example 3). The temperature is then raised to 150° C. at which the reaction mixture is stirred for three hours. After being cooled to ambient temperature, the reaction mixture is poured into ice and then extracted with diethyl ether. The combined extracts are dried over anhydrous magnesium sulfate and filtered. The filtrate is evaporated under reduced pressure, leaving a residue which is purified using column chromatography on silica gel. The product-containing fractions are combined and the solvent evaporated under reduced pressure, leaving 3-(2,2-dimethyl-5-fluoro-7-trifluoromethyl- 1,3-benzodioxol-4-yi)- 1 -methyl-6-trifluoromethyluracil as a residue.

Example 5

SYNTHESIS OF 3-(7-CYANO-2,2-DIMETHYL-5-FLUORO-1,3-BENZODIOXOL-4-YL)-1-METHYL-6-TRI-FLUOROMETHYLURACIL (Compound 15)

In a flask are placed 2.20 g (0.005 mole) of 3-(7-bromo-2,2-dimethyl-5-fluoro- 1,3-benzodioxol-4-yl)- 1 -methyl-6-trifluoromethyluracil, 0.62 g (0.0069 mole) of copper(I) cyanide and 60 mL of N,N-dimethylformamide. The resulting mixture is heated at reflux for 5 hours. This mixture is then cooled and poured into a solution of 2.5 g of hydrated ferric chloride, 0.62 mL of concentrated hydrochloric acid, and 3.8 mL of water. The resulting mixture is maintained at 60-70 °C at which it is stirred for 20 minutes. After being cooled the mixture is extracted with methylene chloride, and the extract is washed with dilute hydrochloric acid. The extract is then dried over anhydrous magnesium sulfate, filtered, and the filtrate is evaporated under reduced pressure, leaving a residue. This residue is passed through a column of silica gel, eluting with ethyl acetate/heptane (1:1 ). The product-containing fractions are combined, and the solvent is evaporated under reduced pressure, leaving 3-(7-cyano-2,2-dimethyl-5-fluoro-1,3-benzodioxol-4-yl)-1-methyl-6-trifluoromethyluracil (Compound 15) as a residue.

HERBICIDAL ACTIVITY

The 3-(bicyclic heterocyclyl)-6-fluoroalkyluracils herbicides of this invention were tested for pre- and postemergence herbicidal activity using a variety of crops and weeds. The test plants included soybean (*Glycine max* var. Williams), field corn (*Zea mays* var. Agway 425X), wheat (*Triticum aestivum* var. Wheaton), morningglory (*Ipomoea lacunosa* or *Ipomoea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellada media*), and common cocklebur (*Xanthium pensylvanicum*).

For preemergence testing, two disposable fiber flats (8 cm×15 cm×25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and Johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for postemergence testing were prepared in the same manner except that they were planted 8-12 days prior to the preemergence flats and were placed in a greenhouse and watered, thus allowing the seeds to germinate and the foliage to develop.

In both pre- and postemergence tests, a stock solution of the candidate herbicide was prepared by dissolving 0.27g of the compound in 20 mL of water/acetone (50/50) containing 0.5% v/v sorbitan monolaurate. For an application rate of 3000 g/ha of herbicide a 10 mL portion of the stock solution was diluted with water/acetone (50/50) to 45 mL. The volumes of stock solution and diluent used to prepare solutions for lower application rates are shown in the following table:

| Application Rate (g/ha) | Volume of Stock Solution (mL) | Volume of Acetone/Water (mL) | Total Volume of Spray Solution (mL) |
|---|---|---|---|
| 3000 | 10 | 35 | 45 |
| 900 | 3 | 42 | 45 |
| 300 | 1 | 44 | 45 |
| 90 | 0.3 | 35 | 45.3 |
| 30 | 0.1 | 45 | 45.1 |
| 9 | 0.03 | 45 | 45.03 |
| 3 | 0.01 | 45 | 45.01 |

The preemergence flats were initially subjected to a light water spray. The four flats were placed two by two along a conveyor belt (i.e., the two preemergence followed by the two postemergence flats). The conveyor belt fed under a spray nozzle mounted about ten inches above the postemergent foliage. The preemergent flats were elevated on the belt so that the soil surface was at the same level below the spray nozzle as the foliage canopy of the postemergent plants. The spray of herbicidal solution was commenced and once stabilized, the flats were passed under the spray at a speed to receive a coverage equivalent of 1000L/ha. At this coverage the application rates are those shown in the above table for the individual herbicidal solutions. The preemergence flats were watered immediately thereafter, placed in the greenhouse and watered regularly at the soil surface. The postemergence flats were immediately placed in the greenhouse and not watered until 24 hours after treatment with the test solution. Thereafter they were regularly watered at ground level. After 17–21 days the plants were examined and the phytotoxicity data were recorded.

Herbicidal activity data at selected application rates are given for various compounds of this invention in Table 2 and Table 3. The test compounds are identified by numbers which correspond to those in Table 1.

Phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Alabama, 1977. The rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application, the 3-(bicyclic heterocyclyl)-6-fluoroalkyluracils are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as watersoluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersants. The wettable powder is ultimately applied to the soil either as a dry dust or as an emulsion in water or other liquid. Typical carriers for wettable powders include Fuller's earth, kaolin clays, silicas, and other highly absorbent, readily wettable inorganic diluents. Wettable powders normally are prepared to contain about 5-80% of active ingredient, depending on the absorbency of the carder, and usually also contain a small amount of a wetting, dispersing or emulsifying agent to facilitate dispersion. For example, a useful wettable powder formulation contains 80.8 parts of the herbicidal compound, 17.9 parts of Palmetto clay, 1.0 part of sodium lignosulfonate, and 0.3 part of sulfonated aliphatic polyester as wetting agents. Frequently additional wetting agent and/or oil will be added to the tank mix for postemergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form by a propellant, such as carbon dioxide, propane or butane, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The 3-(bicyclic heterocyclyl)-6-fluoroalkyluracils of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, for example, about 4 to 300 g/ha to, preferably about 10 to 30 g/ha. For field use, where there are losses of herbicide, higher application rates (for example, four times the rates mentioned above) may be employed.

The 3-(bicyclic heterocyclyl)-6-fluoroalkyluracils of this invention may be used in combination with other herbicides, for example they may be mixed with, say, an equal or larger amount of a known herbicide such as aryloxyalkanoic acid herbicides such as (2,4-dichlorophenoxy)acetic acid (2,4-D), (4-chloro-2-methylphenoxy)acetic acid (MCPA), (±)-2-(4-chloro-2-methylphenoxy)propanoic acid (MCPP); urea herbicides, such as N,N-dimethyl-N'-[4-( 1 -methylethyl)-phenyl]urea (isoproturon); imidazolinone herbicides, such as 2-[4,5-dihydro-4-methyl-4-(1-methylethyl)-5-oxo-1H-imidazol-2-yl]-3-pyridinecarboxylic acid (imazapyr), a reaction product comprising (±)-2-[4,5-dihydro-4-methyl-4-( 1 -methylethyl)-5-oxo-1H-imidazol-2-yl]-4-methylbenzoic acid and (±)-2-[4,5-dihydro-4-methyl-4-( 1 -methylethyl)-5-oxo- 1 H-imidazol-2-yl]-5-methylbenzoic acid (imazamethabenz), (±)-2-[4,5-dihydro-4-methyl-4-( 1 -methylethyl)-5-oxo-1H-imidazol-2-yl]-5-ethyl-3-pyridinecarboxylic acid (imazethapyr),and (±)-2-[4,5-dihydro-4-methyl-4-( 1 -methylethyl)-5-oxo- 1 H-imidazol-2-yl]-3-quinoline-carboxylic acid (imazaquin); diphenyl ether herbicides, such as 5-[2-chloro-4-(trifluoromethyl)phenoxy]-2-nitrobenzoic acid (acifluorfen), methyl 5-(2,4-dichlorophenoxy)-2-nitrobenzoate (bifenox), and 5-[2-chloro-4-(trifluoromethyl)phenoxy]-N-(methylsulfonyl)-2-nitrobenzamide (fomasafen); hydroxybenzonitrile herbicides, such as 4-hydroxy-3,5-diiodobenzonitrile (ioxynil), and 3,5-dibromo-4-hydroxybenzonitrile (bromoxynil); sulfonylurea herbicides, such as 2-[[[[(4-chloro-6-methoxy-2-pyrimidinyl)amino]carbonyl]amino]sulfonyl]benzoic acid (chlorimuron), 2-chloro-N-[[(4-methoxy-6-methyl- 1,3,5-triazin-2-yl)amino]carbonyl]-benzenesulfonamide (chlorsulfuron), 2-[[[[(4,6-dimethoxy-2-pyrimidinyl)amino]carbonyl]amino]sulfonyl]-methyl]benzoic acid (bensulfuron), 2-[[[[(4,6-dimethoxy-2-pyrimidinyl)amino]carbonyl]amino]sulfonyl]-I-methyl-1H-pyrazol-4-carboxylic acid (pyrazosulfuron), 3-[[[[(4-methoxy-6-methyl- 1,3,5-triazin-2-yl)amino]carbonyl]amino]sulfonyl]-2-thiophenecarboxylic acid (thifensulfuron), and 2-(2-chloroethoxy)-N-[[(4-methoxy-6-methyl- 1,3,5-triazin-2-yl)amino]carbonyl]benzenesulfonamide (triasulfuron); 2-( 4-aryloxyphenoxy)alkanoic acid herbicides, such as (±)-2-[4-[(6-chloro-2-benzoxazolyl)oxy]phenoxy]propanoic acid (fenoxaprop), (±)-2-[4-[[5-(trifluoromethyl)-2-pyridinyl]oxy]phenoxy]propanoic acid (fluazifop), (±)-2-[4-(6-chloro-2-quinoxalinyl)oxy]phenoxy]-propanoic acid (quizalofop), and (±)-2-[,(2,4-dichlorophenoxy)phenoxy]propanoic acid (diclofop); benzothiadiazinone herbicides, such as 3-(1-methylethyl)-1H-2, 1,3-benzothiadiazin-4(3H)-one 2,2-dioxide (bentazone); 2-chloroacetanilide herbicides, such as N-(butoxymethyl)-2-chloro-2', 6'-diethylacetanilide (butachlor); arenecarboxylic acid herbicides, such as 3,6-dichloro-2-methoxybenzoic acid (dicamba); and pyridyloxyacetic acid herbicides, such as [(4-amino-3,5-dichloro-6-fluoro-2-pyridinyl)oxy]acetic acid (fluroxypyr).

It is apparent that various modifications may be made in the formulation and application of the compounds of this invention without departing from the inventive concepts herein as defined in the claims.

TABLE 1

3-(Bicyclic heterocyclyl)-6-fluoroalkyluracils

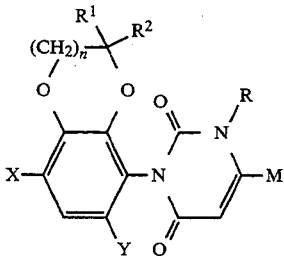

| n | X | Y | R | $R^1$ | $R^2$ | M |
|---|---|---|---|---|---|---|
| 1 | 0 | H | F | $CH_3$ | $CH_3$ | $CH_3$ | $CF_3$ |
| 2 | 0 | F | H | $CH_3$ | $CH_3$ | $CH_3$ | $CF_3$ |
| 3 | 0 | F | F | $CH_3$ | $CH_3$ | $CH_3$ | $CF_3$ |
| 4 | 0 | Cl | H | $CH_3$ | $CH_3$ | $CH_3$ | $CF_3$ |
| 5 | 0 | Cl | F | $CH_3$ | $CH_3$ | $CH_3$ | $CF_3$ |
| 6 | 0 | Cl | F | $C_2H_5$ | $CH_3$ | $CH_3$ | $CF_3$ |
| 7 | 0 | Cl | F | $CH_2C\equiv CH$ | $CH_3$ | $CH_3$ | $CF_3$ |
| 8 | 0 | Cl | F | $CH_2CN$ | $CH_3$ | $CH_3$ | $CF_3$ |
| 9 | 0 | Cl | F | $CH_3$ | $C_2H_5$ | $CH_3$ | $CF_3$ |
| 10 | 0 | Cl | F | $CH_3$ | $C_2H_5$ | $C_2H_5$ | $CF_3$ |
| 11 | 0 | Cl | F | $CH_3$ | $CH_3$ | $CH_3$ | $C_2F_5$ |
| 12 | 0 | $CH_3$ | F | $CH_3$ | $CH_3$ | $CH_3$ | $CF_3$ |
| 13 | 0 | $CF_3$ | F | $CH_3$ | $CH_3$ | $CH_3$ | $CF_3$ |
| 14 | 0 | CN | H | $CH_3$ | $CH_3$ | $CH_3$ | $CF_3$ |
| 15 | 0 | CN | F | $CH_3$ | $CH_3$ | $CH_3$ | $CF_3$ |
| 16 | 0 | Cl | Cl | $CH_3$ | $CH_3$ | $CH_3$ | $CF_3$ |
| 17 | 0 | Br | F | $CH_3$ | $CH_3$ | $CH_3$ | $CF_3$ |
| 18 | 1 | F | H | $CH_3$ | H | H | $CF_3$ |
| 19 | 1 | F | F | $CH_3$ | H | H | $CF_3$ |
| 20 | 1 | Cl | H | $CH_3$ | H | H | $CF_3$ |
| 21 | 1 | Cl | F | $CH_3$ | H | H | $CF_3$ |
| 22 | 1 | Cl | F | $C_2H_5$ | H | H | $CF_3$ |
| 23 | 1 | Cl | F | $CH_3$ | H | H | $C_2F_5$ |
| 24 | 1 | Cl | F | $CH_2C\equiv CH$ | H | H | $CF_3$ |
| 25 | 1 | Cl | F | $CH_2CN$ | H | H | $CF_3$ |
| 26 | 1 | Cl | Cl | $CH_3$ | H | H | $CF_3$ |
| 27 | 1 | Br | F | $CH_3$ | H | H | $CF_3$ |

TABLE 1-continued 3-(Bicyclic heterocyclyl)-6-fluoroalkyluracils

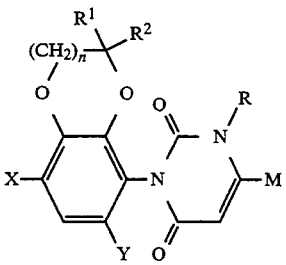

| n | X | Y | R | R$^1$ | R$^2$ | M |
|---|---|---|---|---|---|---|
| 28 | 1 | CH$_3$ | F | CH$_3$ | H | H | CF$_3$ |
| 29 | 1 | CF$_3$ | F | CH$_3$ | H | H | CF$_3$ |
| 30 | 1 | CN | H | CH$_3$ | H | H | CF$_3$ |
| 31 | 1 | CN | F | CH$_3$ | H | H | CF$_3$ |

TABLE 2

Characterizing Properties

| Compound No | MP (°C.) |
|---|---|
| 1 | oil |
| 5 | oil |
| 17 | oil |
| 20 | 205–207 |
| 21 | 186–190 |
| 26 | 173–176 |
| 27 | 168–170 |

TABLE 3

PREEMERGENCE HERBICIDAL ACTIVITY (% CONTROL)

| Compound No. | 1 | 5 | 17 | 21 | 27 |
|---|---|---|---|---|---|
| Rate (kg/ha) | 0.1 | 0.1 | 0.1 | 0.1 | 0.1 |
| Species |   |   |   |   |   |
| Soybean | 75 | 100* | 100 | 100** | 100 |
| Wheat | 0 | 100* | 100 | 100** | 90 |
| Corn | 75 | 100* | 100 | 100** | 100 |
| Velvetleaf | 100 | 100* | 100 | 100** | 100 |
| Morningglory | 100 | 100* | 100 | 100** | 100 |
| Chickweed | 10 | 100 | 100 | 100** | 100 |
| Cocklebur | 30 | 100* | 100 | 100** | 100 |
| Blackgrass | 0 | 100* | 100 | 95** | 90 |
| Green foxtail | 100 | 100* | 100 | 100** | 100 |
| Johnsongrass | 80 | 100* | 100 | 100** | 100 |

*Average of three results
**Average of two results

TABLE 4

POSTEMERGENCE HERBICIDAL ACTIVITY (% CONTROL)

| Compound No. | 1 | 5 | 17 | 21 | 27 |
|---|---|---|---|---|---|
| Rate (kg/ha) | 0.1 | 0.1 | 0.1 | 0.1 | 0.1 |
| Species |   |   |   |   |   |
| Soybean | 80 | 100* | 100 | 100 | 100 |
| Wheat | 0 | 95* | 95 | 70 | 65 |
| Corn | 50 | 100* | 90 | 90 | 85 |
| Velvetleaf | 100 | 100* | 100 | 100 | 100 |
| Morningglory | 100 | 100* | 100 | 100 | 100 |
| Chickweed | 0 | 100 | 100 | 100 | 75 |
| Cocklebur | 40 | 100* | 100 | 100 | 95 |
| Blackgrass | 0 | 100* | 100 | 85 | 40 |
| Green foxtail | 40 | 100* | 100 | 100 | 100 |
| Johnsongrass | 40 | 100* | 100 | 100 | 95 |

*Average of three results

We claim:

1. A compound of the formula:

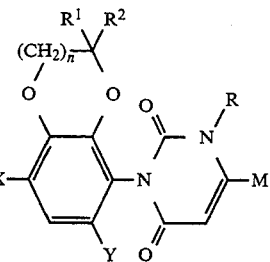

in which

M is fluoroalkyl(C$_{1-6}$); R is hydrogen, alkyl(C$_{1-6}$), 2-alkynyl(C$_{3-6}$); 2-alkenyl(C$_{3-6}$,), or cyanoalkyl(C$_{1-6}$); R$^1$ is hydrogen or alkyl(C$_{1-6}$); R$^2$ is hydrogen or alkyl(C$_{1-6}$); Y is hydrogen, fluorine, chlorine, or bromine; X is hydrogen, fluorine, chlorine, bromine, cyano, alkyl(C$_{1-6}$), or fluoroalkyl(C$_{1-6}$); and n is 0 or 1.

2. A compound of claim 1 in which
M is fluoroalkyl(C$_{1-3}$); R is hydrogen, alkyl(C$_{1-3}$), 2-alkynyl(C$_{3-4}$); 2-alkenyl(C$_{3-4}$), or cyanoalkyl(C$_{1-3}$); R$^1$ is hydrogen or alkyl(C$_{1-3}$); R$^2$ is hydrogen or alkyl(C$_{1-3}$); Y is hydrogen, fluorine, chlorine, or bromine; X is hydrogen, fluorine, chlorine, bromine, cyano, alkyl(C$_{1-3}$), or fluoroalkyl(C$_{1-3}$); and n is 0 or 1.

3. A compound of claim 2 in which M is fluoromethyl or fluoroethyl; R is hydrogen, methyl, ethyl, 2-alkynyl(C$_3$), 2-alkenyl(C$_3$), or cyanomethyl; R$^1$ is hydrogen, methyl, or ethyl; R$^2$ is hydrogen, methyl, or ethyl; Y is hydrogen, fluorine, chlorine, or bromine; X is hydrogen, fluorine, chlorine, bromine, cyano, methyl, or fluoromethyl; and n is 0 or 1.

4. A compound of claim 3 in which M is trifluoromethyl or pentafluoroethyl; R is methyl; R$^1$ is hydrogen, methyl, or ethyl; R$^2$ is hydrogen, methyl, or ethyl; Y is hydrogen, fluorine, or chlorine; X is chlorine or bromine; and n is 0 or 1.

5. A compound of claim 4 in which M is trifluoromethyl; R is methyl; R$^1$ is hydrogen or methyl; R$^2$ is hydrogen or methyl; X is chlorine or bromine; Y is hydrogen, fluorine, or chlorine; and n is 0 or 1.

6. The compound of claim 1 which is 3-(7-chloro-2,2-dimethyl-5-fluoro- 1,3-benzodioxol-4-yl)- 1 -methyl-6-trifluoromethyluracil.

7. The compound of claim 1 which is 3-(7-bromo-2,2-dimethyl-5-fluoro- 1,3-benzodioxol-4yl)- 1 -methyl-6-trifluoromethyluracil.

8. The compound of claim 1 which is 3-(8-chloro-1,4-benzodioxan-5-yl)- 1 -methyl-6-trifluoromethyluracil.

9. The compound of claim 1 which is 3-(8-bromo-6-fluoro-1,4-benzodioxan-5-yl)- 1 -methyl-6-trifluoromethyluracil.

10. The compound of claim 1 which is 3-(6,8-dichloro-1,4-benzodioxan-5-yl)- 1 -methyl-6-trifluoromethyluracil.

11. The compound of claim 1 which is 3-(7-chloro-2,2-dimethyl-1,3-benzodioxol-4-yl)- 1 -methyl-6-trifluoromethyluracil.

12. A composition for controling undesired plant growth comprising an herbicidally effective amount of a compound of claim 1 in admixture with an agriculturally acceptable carrier.

13. A method for controlling undesired plant growth which comprises applying to a locus where control is desired, an herbically effective amount of the composition of claim 12.

* * * * *